(12) United States Patent
Kanougi et al.

(10) Patent No.: US 7,285,688 B2
(45) Date of Patent: Oct. 23, 2007

(54) PROTON TYPE β ZEOLITE, PREPARATION METHOD THEREOF AND PROCESS FOR PREPARING PHENOL COMPOUND USING THE SAME

(75) Inventors: Tomonori Kanougi, Ichihara (JP); Takashi Atoguchi, Ichihara (JP); Shigeru Yao, Ichihara (JP)

(73) Assignee: UBE Industries, Ltd., Ube-shi, Yamaguchi (JP)

( * ) Notice: Subject to any disclaimer, the term of this patent is extended or adjusted under 35 U.S.C. 154(b) by 482 days.

(21) Appl. No.: 10/856,886

(22) Filed: May 27, 2004

(65) Prior Publication Data

US 2004/0242938 A1  Dec. 2, 2004

(30) Foreign Application Priority Data

| May 30, 2003 | (JP) | ............................. 2003-153842 |
| Jul. 30, 2003 | (JP) | ............................. 2003-282286 |
| Sep. 1, 2003 | (JP) | ............................. 2003-308366 |

(51) Int. Cl.
   *C07C 27/10*   (2006.01)
(52) U.S. Cl. .................................... 568/700
(58) Field of Classification Search ................. 568/631
   See application file for complete search history.

(56) References Cited

U.S. PATENT DOCUMENTS

| 3,580,956 A | 5/1971 | Bloch et al. |
| 4,578,521 A | 3/1986 | Chang et al. |
| 6,025,293 A | 2/2000 | Wu et al. |
| 6,441,250 B2 * | 8/2002 | Atoguchi et al. ........... 568/771 |

FOREIGN PATENT DOCUMENTS

| FR | 2 693 457 A | 1/1994 |
| JP | 3-128336 A | 5/1991 |
| JP | 9-151151 A | 6/1997 |
| JP | 2003-26623 A | 1/2003 |

(Continued)

OTHER PUBLICATIONS

Roberge, D.M. et al., "Dealumination of Zeolite Beta by Acid Leaching: A New Insight with Two-dimensional Muti-quantum and Cross Polarization $^{27}$Al MAS NMR," *Physical Chemistry Chemical Physics*, Royal Society of Chemistry, Cambridge BG, vol. 4, No. 13, Jul. 1, 2002, pp. 3128 to 3135.

(Continued)

*Primary Examiner*—Johann Richter
*Assistant Examiner*—Kellette Gale
(74) *Attorney, Agent, or Firm*—Frishauf, Holtz, Goodman & Chick, P.C.

(57) ABSTRACT

Disclosed are a proton type β zeolite in which an acid site showing a desorption peak with a range of ±100° C. with a center of 330° C. exists in a spectrum measured by the ammonia temperature programmed desorption method ($NH_3$-TPD), and an amount of a strong acid site showing a desorption peak of 500° C. or higher is controlled to 2.5 μmol/g or less, a method for preparing the same, and a process for preparing a phenol compound by oxidizing a benzene compound with a peroxide in the presence of the proton type β zeolite.

15 Claims, 3 Drawing Sheets

A: Main peak with center of 330°C
B: Desorption peak at 500°C or higher

FOREIGN PATENT DOCUMENTS

JP          2003026623 A  *  1/2003

OTHER PUBLICATIONS

Camiloti, A.M. et al., "Acidity of Beta Zeolite Determined by TPD of Ammonia and Ethylbenzene Disproportionation," *Applied Catalysis A: General*, Elsevier Science, Amsterdam, NL, vol. 182, No. 1, Jun. 7, 1999, pp. 107 to 113.

"13901 Chemicals", *The Chemical Daily Co., Ltd., Japan*, p. 653 (2001).

B. Notari, "Microporous Cystalline Titanium Silicates", *Advances in Catalysis*, vol. 41, pp. 253-334 (1996).

R.A. Sheldon et al, "Heterogeneous Catalysts for Liquid Phase Oxidations: . . . ", *Acc. Chem. Res.*, 31(8) , pp. 485-493 (1998).

U. Wilkenhöner et al, "Influence of Pore and Crystal Size of Crystalline Titanosilicates . . . ", *Journal of Catalysis*, 203, pp. 201-212 (2001).

T. Tezuka et al, "Isomer Distribution Ratios of Phenols in Aromatic Hydroxylation . . . ", *J.Am. Chem. Soc.*, vol. 103, pp. 3045-3049 (1981).

M. Sako et al, "Photo-oxygenation of Benzene Derivatives by a Novel Derivative . . . ", *J. Chem. Soc. Perkin Trans.*, vol. 1, pp. 863-867 (1990).

A. Bhaumik et al, "Titanium Silicate Molecular Sieve . . .", *J.Chem. Soc.*, Chem. Comm., vol. 3, pp. 349-350 (1995).

A. Nasreen et al, "Aromatic Hydroxylation By A New Cupric Nitrate-$H_2O_2$-Phosphate Buffer System", *Organic Prep. & Proc. Int.*, vol. 32, pp. 373-405 (2000).

X. Zaiku et al, "Influence of Citric Acid Treatment on the Surface of Zeolite Beta", *J. Phys. Chem. B.*, vol. 104, No. 13, pp. 2853-2859 (2000).

Y. Miyamoto et al, "Acidity of β zeolite with different $Si/Al_2$ ratio as measured by temperature programmed desorption of ammonia", *Microporous and Mesoporous Materials*, 40, pp. 271-281 (2000).

Keulemans, "Gas Chromatography", *Reinhold*, p. 39 (1957).

* cited by examiner

Fig. 1

A: Main peak with center of 330°C
B: Desorption peak at 500°C or higher

PROTON TYPE β ZEOLITE, PREPARATION METHOD THEREOF AND PROCESS FOR PREPARING PHENOL COMPOUND USING THE SAME

BACKGROUND OF THE INVENTION

1. Technical Field

The present invention relates to a novel proton type β zeolite and a preparation method thereof, and a process for preparing a phenol compound by oxidating a benzene compound such as a phenol compound or phenyl ether, etc. by a peroxide in the presence of the above zeolite and a ketone or a carboxylic acid.

2. Prior art

In a hydroxyphenyl ether represented by the following formula (a) obtained by the process for preparing a phenol compound of the present invention, for example, o-methoxy-phenol (guaiacol) in which $R^1$ is a methyl group has been used as a starting material for medicine or perfume (13901 Chemicals, published by The Chemical Daily Co., Ltd., Japan, 2001, p. 653), and p-methoxyphenol is an important compound used as an antioxidant or a starting material for a medicine, etc. (Japanese Unexamined Patent Publication No. Hei. 9-151151).

(a)

wherein R' represents an alkyl group having 1 to 5 carbon atoms.

As a technique to produce a dihydric phenol compound by oxidizing a phenol compound using zeolite as a catalyst, for example, there is an example in which faujasite or mordenite containing a rare earth metal is used is disclosed in U.S. Pat. No. 3,580,956, and an example in which in proton type ZSM-5 is used is disclosed in U.S. Pat. No. 4,578,521. Also, in French Unexamined Patent Publication No. 2,693,457, natural zeolite such as chabazite, etc., or synthetic zeolite such as US-Y, ZSM-5, etc. have been reported. However, in these techniques, yield of the objective product were not sufficient. Also, there is no description about a relationship between the strength of an acid site existing on these zeolites and a catalyst activity in the production of a dihydric phenol.

In "Advances in Catalysis", vol. 41 (1996), pp. 253-334, an example using TS-1 (titanium is contained in the lattice of ZSM-5) has been described. However, as shown in Accounts of Chemical Research, 31 (8), (1998) pp. 485-493, TS-1 involves problems in preparation reproducibility frequently, and also yield of the objective product is not sufficient.

Also, in the "Journal of Catalysis", vol. 203, (2001) pp. 201-212, a comparison of β zeolite containing TS-1 or titanium in the lattice is described, but for the β zeolite containing TS-1, the yield thereof based on an amount of hydrogen peroxide as a standard is 71.5%, and in the β zeolite containing titanium, it is 62.8%, so that their yields are not sufficient.

In U.S. Pat. No. 6,441,250 and Japanese Unexamined Patent Publication No. 2003-26623, there is described an example that uses β zeolite, and further disclosed that β zeolite into which an alkali metal ion has been introduced is used, yield of a dihydric phenol compound is improved. However, in the β zeolite disclosed in these references, temperature dependency with regard to a reaction yield is high, and yield at a lower temperature side of 90° C. or lower is insufficient. Accordingly, a temperature range is limited when the reaction is practically carried out, so that a further improvement has been desired.

On the other hand, in the reaction of producing a hydroxyphenyl ether with one step by oxidizing a phenyl ether, o-hydroxyphenyl ether in which the ortho-position has been oxidized and p-hydroxyphenyl ether in which the para-position has been oxidized are generally produced simultaneously (see, for example, Journal of American Chemical Society, vol. 103 (1981), pp. 3045-3049, Journal of Chemical Society Perkin Transition, vol. 1, No. 6 (1990), pp. 863-867, Journal of Chemical Society, Chemical Communications, vol. 3 (1995), pp. 349-350). Utilizability in industry of hydroxyphenyl ether may differ depending on its manner of substitution, in particular, it is markedly different from each other in an ortho-position substituted material and a para-position substituted material. For example, o-methoxyphenol is important as a starting material for medicine or perfume, and p-methoxyphenol is important as an antioxidant (see Japanese Unexamined Patent Publication No. Hei. 9-151151 and "13901 Chemicals", published by The Chemical Daily Co., Ltd., Japan, 2001, p. 653).

Accordingly, when these materials are produced in combination, there are problems not only in yield thereof but also a formed ratio of the ortho-position substituted material and the para-position substituted material. Thus, the respective techniques to predominantly produce the ortho-position substituted material or the para-position substituted material are each important.

As a technique to predominantly produce the ortho-position substituted material or the para-position substituted material by oxidizing a phenyl ether to produce a hydroxyphenyl ether with one step, the following may be mentioned.

Of these, as a technique to use a homogeneous catalyst, in "13901 Chemicals", published by The Chemical Daily Co., Ltd., Japan, 2001, p. 653, there is described a method for producing methoxyphenol that oxidizes anisole by hydrogen peroxide in the presence of manganese polynitroporphyline as a catalyst. In this method, yield of the methoxyphenol based on the hydrogen peroxide is as high as 98%, and whereas it shows a high para-position selectivity (a formation ratio of the ortho-position substituted material/the para-position substituted material (hereinafter referred to as an o/p ratio) of 0.11, it is difficult to obtain the catalyst with a large amount, as well as there are problems that recovery and reuse of the catalyst are difficult, so that it involves a problem when an industrial production is considered.

In Organic Preparations and Procedures Int., vol. 32 (2000), pp. 373-405, there is disclosed a preparation method of methoxyphenol from anisole using hydrogen peroxide as an oxidizing agent and copper nitrate as a catalyst. In this method, the reaction is carried out by controlling a pH of the reaction system with a phosphate buffer, whereby a high yield of 94% is accomplished as yield of the methoxyphenol based on anisole, and a high para position selectivity is obtained as an o/p ratio=0.12. However, this is a homogeneous system reaction so that recovery of the catalyst is difficult and an extremely large amount of a solvent is required, so that the procedure such as recovery thereof is complicated and trouble-some when an industrial production thereof is considered.

As a technique using a heterogeneous catalyst, in Journal of Chemical Society Chemical Communications, vol. 3 (1995), pp. 349-350, a process for preparing methoxyphenol which comprises oxidizing anisole with hydrogen peroxide by using TS-1 containing titanium in the lattice has been described. In this method, yield of the methoxyphenol based on the anisole is 67%, and an o/p ratio=0.35. As shown in the above-mentioned literature, TS-1 involves a problem in its preparation reproducibility in many times and a reaction yield is not sufficient.

In Japanese Unexamined Patent Publication No. Hei. 3-128336, a process for preparing methoxyphenol by oxidizing anisole using a catalyst system in which an alkali metal salt of a protonic acid such as sulfuric acid, etc. and an oxy acid of phosphor such as ortho phosphoric acid, etc. has been described, but there is no description about zeolite.

In French Patent Laid-Open Publication No. 2,693,457, a process for preparing methoxyphenol by oxidizing anisole by using US-Y zeolite as a proton type zeolite in the presence of a ketone has been described, but there is no description about a proton type β zeolite, and its catalyst characteristics are unknown. Also, as a result of a trace test thereof by the inventors, yield of the methoxyphenol was 47.1% (o/p ratio=2.86) so that it was insufficient (see Comparative example 7).

On the other hand, for example, in Journal of American Chemical Society, vol. 103 (1981), pp. 3045-3049, a process for preparing methoxyphenol from anisole by photooxidation using a peroxide of an azo type compound as an oxidizing agent has been described. In this process, an ortho-position substituted material is predominantly formed (a formation ratio of the ortho-position substituted material/the para-position substituted material (hereinafter referred to an o/p ratio)=1.78), but yield of the objective compound based on the oxidizing agent is 30% or so. Also, in Journal of Chemical Society Perkin Transition, 1, vol. 6 (1990), p. 863-867, a process for preparing methoxyphenol from anisole by photooxidation using an N-oxide compound having a heterocyclic structure as an oxidizing agent has been described. In this process, an ortho-position substituted material is predominantly formed (o/p ratio=1.47), but yield of the methoxyphenol based on the oxidizing agent is 42% or so in the whole yield. In these techniques, there is a merit that the reaction proceeds without any catalyst, but there is a problem that yield of the objective product is insufficient while an expensive oxidizing agent is used.

As described above, with regard to the technique to oxidize an ortho-position substituted material predominantly, there are reports in which yield of the hydroxyphenyl ether based on the oxidizing agent is 40% or so, and a technique which gives a hydroxyphenyl ether with a high yield has not yet been found out.

SUMMARY OF THE INVENTION

An object of the present invention is to provide a novel proton type β zeolite that can be easily and simply prepared and shows high reactivity at a lower temperature side, a preparation method thereof and a process for producing a para-position substituted and/or an orthoposition substituted phenol compound industrially by oxidizing a benzene compound such as a phenol compound or a phenyl ether compound, etc. with a peroxide using the same to produce a phenol compound with a high yield.

The present inventors have studied to solve the above-mentioned problems, and as a result, they have found a novel proton type β zeolite, and by using the zeolite, they have also found an industrial process for preparing a para-position substituted and/or ortho-position substituted phenol compound by oxidizing a benzene compound such as a phenol compound or phenyl ether compound, etc. with a peroxide to produce para-position substituted and/or ortho-position substituted phenol compound with a high yield to accomplish the present invention.

That is, the present invention is as follows.

The first invention relates to a proton type β zeolite in which an acid site showing a desorption peak with a range of ±100° C. with a center of 330° C. exists in a spectrum measured by the ammonia temperature programmed desorption method ($NH_3$-TPD), and an amount of a strong acid site showing a desorption peak of 500° C. or higher is controlled to 2.5 μmmol/g or less.

The second invention relates to a method for preparing the proton type β zeolite according to the first invention which comprises immersing β zeolite having an atomic ratio of Al:Si being 1:25 to 1:10000 in an aqueous acidic solution having a pH of 0.01 to 6.0, preferably a pH of 0.5 to 4.0, then washing, drying and calcinating the same in this order.

The third invention relates to a process for preparing at least one of phenol compounds selected from the group consisting of a compound represented by the formulae (3) and (4):

(3)

(4)

wherein $R^1$ represents a hydroxyl group, a straight or branched alkyl group having 1 to 6 carbon atoms or a straight or branched alkoxy group having 1 to 6 carbon atoms, $R^2$ represents a hydrogen atom, a straight or branched alkyl group having 1 to 6 carbon atoms, a straight or branched alkoxy group having 1 to 6 carbon atoms or a halogen atom, n is an integer of 0 to 5, m is an integer of 0 to 5, n+m=0 to 5, a plural number of $R^1$ or $R^2$ may be the same or different from each other, $R^3$ represents a hydrogen atom, a straight or branched alkyl group having 1 to 6 carbon atoms, a straight or branched alkoxy group having 1 to 6 carbon atoms or a halogen atom, p is an integer of 1 or 2 and q is an integer of 0 to 3, which comprises oxidizing at least one of benzene compounds represented by the formulae (1) and (2):

(1)

-continued (2)

wherein $R^1$, $R^2$, $R^3$, n, m, p and q have the same meanings as defined above, with a peroxide in the presence of the proton type β zeolite according to the first invention, and in the presence of a ketone or a carboxylic acid.

DESCRIPTION OF THE PREFERRED EMBODIMENTS

The proton type β zeolite of the present invention can be obtained by immersing β zeolite in an aqueous acidic solution, and after taking out the treated β zeolite from the aqueous acidic solution, washing, drying and calcinating the same in this order.

Here, as the β zeolite, β zeolite having an atomic ratio of Al:Si being 1:25 to 1:10000 is preferably used. Incidentally, this ratio can be controlled by the composition of a Si compound and an Al compound which are starting materials for the β zeolite, for example, by the composition of sodium silicate and sodium aluminate.

As the β zeolite, a proton type β zeolite, an ammonium ion-exchanged type β zeolite, an alkali metal ion-exchanged type β zeolite or the like which have not been subjected to a treatment with an aqueous acidic solution according to the present invention may be used.

The proton type β zeolite can be prepared by the method as disclosed in Journal of Physical Chemistry, 104 (2000), pp. 2853 to 2859. For example, according to the method as disclosed in the above literature, a β zeolite (hereinafter referred to as AS (as-synthesized) β zeolite) obtained by subjecting a silicon source (silica gel, etc.), an aluminum source (sodium aluminate, pseudo boehmite, etc.), and an alkyl ammonium (tetraethyl ammonium hydroxide, etc.) as starting materials to hydrothermal synthesis and then calcination is subjected to heat treatment in an ammonium ion-containing aqueous solution (ammonium salt concentration: 0.1 to 40% by weight) such as ammonium nitrate, ammonium chloride, etc., at 20 to 120° C. for 1 to 20 hours, washed with deionized water, etc., dried at 20 to 150° C., and then, calcinated at 300 to 650° C. for 1 to 10 hours. Or else, a proton type β zeolite obtained by immersing the above-mentioned AS β zeolite in 0.01N to 1N aqueous hydrochloric acid solution, treating at a temperature between room temperature and 100° C. for several minutes to several days, then, washing with deionized water, etc., drying at room temperature to 150° C., and calcinating at 150° C. to 650° C. may be preferably used.

Incidentally, the AS β zeolite may be prepared by the method described in the above-mentioned literature, or a commercially available material may be preferably used.

A content of the aluminum (aluminum in the skeleton) in AS β zeolite is preferably a ratio in which Al:Si (atomic ratio) becomes 1:25 to 1:10000. Incidentally, this ratio can be controlled by changing a composition of a Si compound and an Al compound which are starting materials for the AS β zeolite, for example, sodium silicate and sodium aluminate.

As the ammonium ion exchange type β zeolite, a commercially available material may be used. Also, as the alkali metal ion-exchanged type β zeolite, it can be prepared by the method as disclosed in "Catalyst Preparation Chemistry", published by Kodansha, Japan (1980) pp. 61-73, in which a proton type β zeolite is immersed in the above-mentioned metal ion-containing aqueous solution such as a nitrate, a hydrochloride or a sulfate of the alkali metal.

Of these β zeolites, proton type β zeolite which has not been subjected to a treatment with an aqueous acidic solution according to the present invention is preferably used.

The acid to be used in the aqueous acidic solution of the present invention is not specifically limited, and there may be mentioned an organic acid such as an aliphatic carboxylic acid (formic acid, acetic acid, propionic acid, citric acid, etc.), an aromatic carboxylic acid (benzoic acid, etc.), an amino acid (aspartic acid, glutamic acid, etc.), or a sulfonic acid (trifluoromethylsulfonic acid, etc.), etc., or an inorganic acid (nitric acid, phosphoric acid, hydrofluoric acid, hydrochloric acid, sulfuric acid, etc.), preferably an inorganic acid, more preferably nitric acid.

As the above-mentioned aqueous acidic solution, that adjusted to a pH of 0.01 to 6.0, preferably a pH of 0.5 to 4.0 is used. Also, an amount thereof to be used is not specifically limited so long as the above-mentioned β zeolite is immersed sufficiently.

A temperature to immerce the β zeolite of the present invention in an aqueous acidic solution is preferably in the range of a room temperature to 120° C., more preferably 40 to 90° C.

Also, an immersing time is preferably 1 to 12 hours.

This immersing operation is preferably carried out under stirring, but even when it is allowed to stand, a sufficient effect as above can be obtained.

Next, the β zeolite immersed in the aqueous acidic solution is taken out and washed with water. Here, a method of taken out is not specifically limited, and, for example, it is carried out by a method such as filtration, etc. Also, as water to be used for washing, deionized water is preferably used.

The above-mentioned washed β zeolite is then dried.

A temperature range for drying is preferably 90 to 150° C. A drying time may vary depending on an amount of the above-mentioned β zeolite, and it is preferably 1 hour to 2 days.

After the drying, the above-mentioned β zeolite is subjected to calcination treatment. A temperature range for calcination is preferably 350 to 950° C., more preferably 450 to 850° C.

The calcination time is preferably 1 to 24 hours.

The proton type β zeolite of the present invention obtained by subjecting to the above-mentioned aqueous acidic solution treatment has the characteristics that a spectrum measured by the ammonia temperature programmed desorption method ($NH_3$-TPD, Temperature raising rate: 20°

Figure 2:
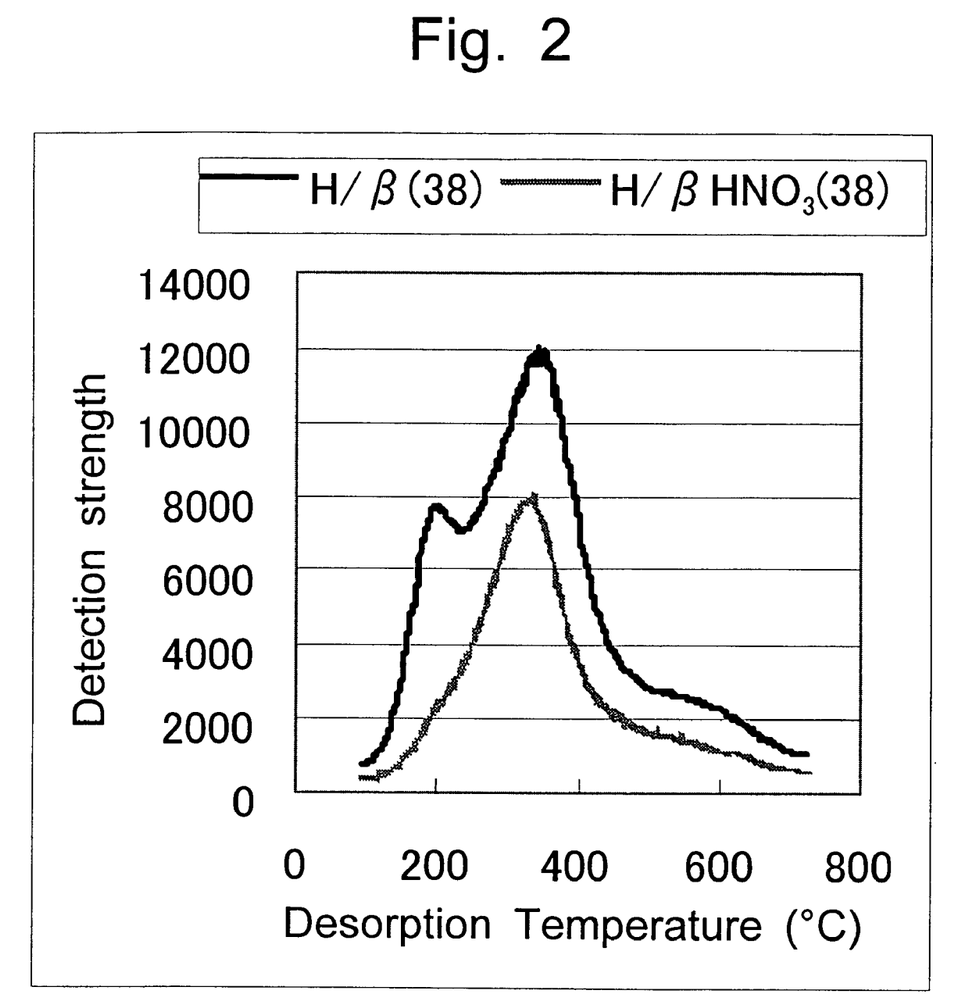
FIG. 2 is a spectrum of H/β (38) and H/β $HNO_3$ (38) by the ammonia temperature programmed desorption method ($NH_3$-TPD).

C./minute, Measured range: 100° C. to 700° C.) is compared with those of a spectrum of non-treated material, an acid site showing a desorption peak with a range of ±100° C. with a center of 330° C. exists, and an amount of the strong acid site showing a desorption peak of 500° C. or higher is 2.5 mmol/g or less, more preferably 0.0005 μmol/g (calculated from a detection limit of the desorption peak) or more, and 2.5 μmol/g or less. Incidentally, a desorption peak near to 200° C. of an untreated material is derived from physically adsorbed ammonia existing on a β zeolite structure and based on a dispersion force, etc., and is markedly lowered by an aqueous acidic solution (see FIG. 2).

Here, an amount of the strong acid site is calculated from an amount of desorbed ammonia in the above-mentioned ammonia temperature programmed desorption method ($NH_3$-TPD) (see Microporous and Mesoporous Materials, 40 (2000) pp. 271-281).

Figure 1:
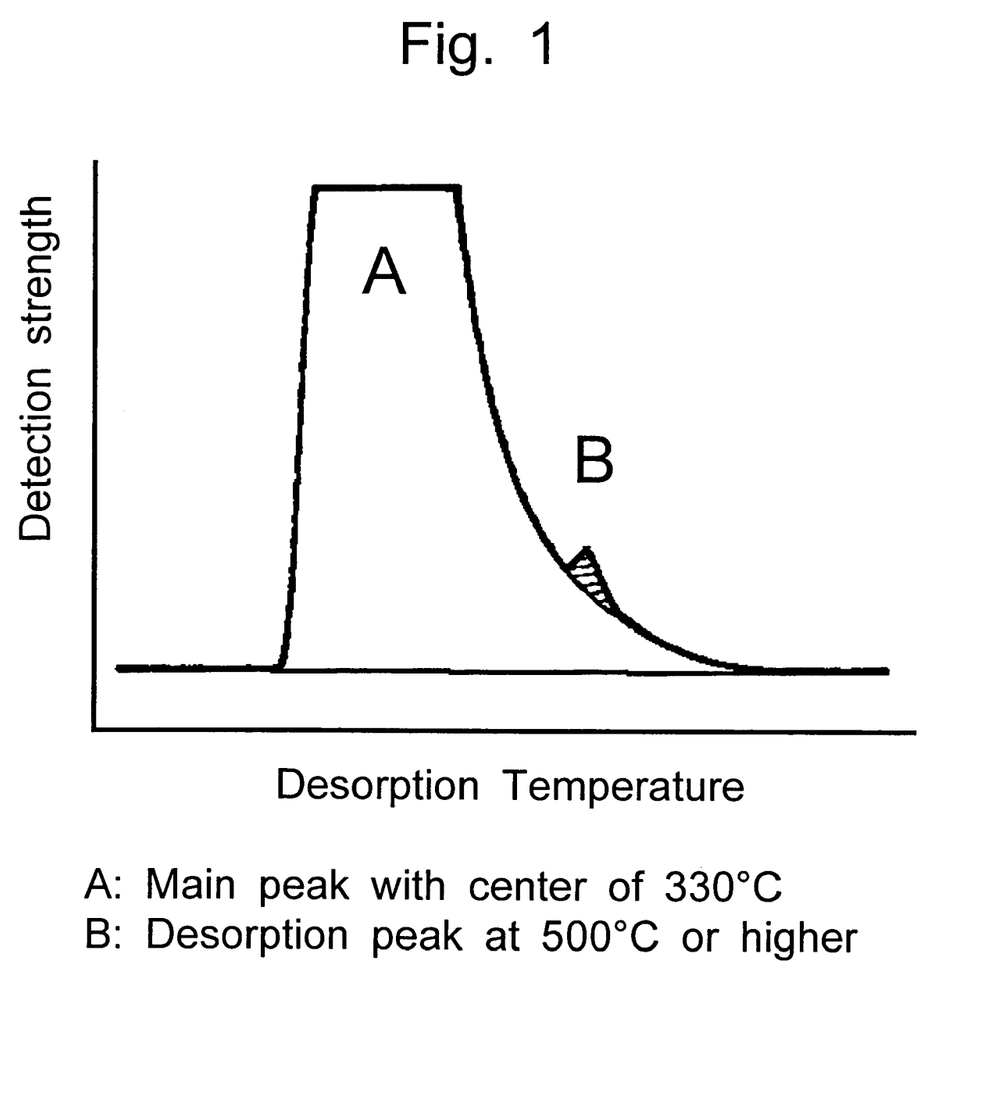
FIG. 1 is a spectrum (a schematic drawing) of proton type β zeolite by the ammonia temperature programmed desorption method ($NH_3$-TPD).

Also, calculation of the amount of the desorbed ammonia is carried out in accordance with a determination method described in Keulemans, "Gas Chromatography", Reinhold, New York, 1957, p. 39, a desorption peak of 500° C. or higher which is on a foot portion of a main peak with a center of 330° C. is punctuated by an extension line of the above mentioned main peak, and quantitated by the surface area. (see FIG. 1 and the following formula 1)

Amount of strong acid site≦($NH_3$—amount of total desorbed ammonia at 100° C. to 700° C. measured by TPD)×{(surface area of B)÷(surface area of A+surface area of B)} wherein A represents a main peak with a center at 330° C., and B represents a desorption peak of 500° C. or higher. See FIG. 1.

Figure 3:
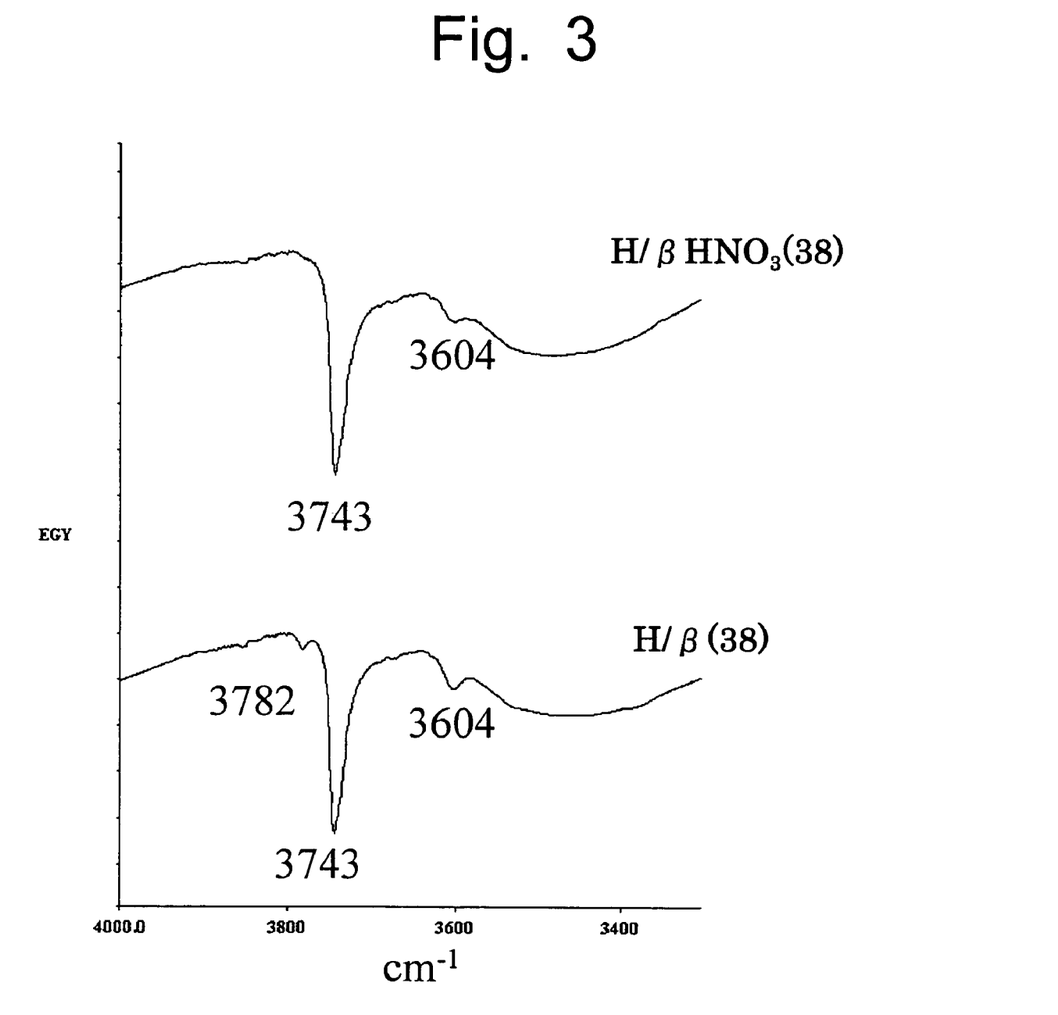
FIG. 3 is a FT-IR spectrum of H/β (38) and H/P $HNO_3$ (38).

Also, the proton type β zeolite of the present invention has a characteristic feature that an absorption at 3782 $cm^{-1}$, is a detection limit or less when its FT-IR spectrum is compared to that of non-treated zeolite (see FIG. 3).

Next, the process for producing a para-position substituted and/or an ortho-position substituted phenol compound using the proton type β zeolite of the present invention is explained.

In the above formula (1), $R^1$ represents a hydroxyl group, a straight or branched alkyl group having 1 to 6 carbon atoms or a straight or branched alkoxy group having 1 to 6 carbon atoms.

As the straight or branched alkyl group having 1 to 6 carbon atoms of $R^1$, there may be mentioned, for example, a methyl group, an ethyl group, a propyl group, a butyl group, a pentyl group and a hexyl group. Incidentally, these groups may include an isomer. Also, as the straight or branched alkoxy group having 1 to 6 carbon atoms of $R^1$, there may be mentioned, for example, a methoxy group, an ethoxy group, a n-propoxy group, an isopropoxy group, a n-butoxy group, a t-butoxy group, etc. Incidentally, these substituents include other structural isomers. In the formula (1), n is preferably an integer of 0 to 3, more preferably 0 or 1.

In the above-mentioned formula (1), when $R^1$ is a hydroxyl group and n=1, it is a phenol compound.

The proton type β zeolite of the present invention is preferably used in the preparation of a dihydric phenol compound, which comprises oxidizing a phenol compound with a peroxide in the presence of a ketone.

As the phenol to be used here, there may be mentioned, for example, phenol in which $R^2$ are all hydrogen atoms, a monovalent monoalkylphenol, a monovalent halogenated phenol and a monovalent polyalkylphenol in which at least one of $R^2$ is a straight or branched alkyl group having 1 to 6 carbon atoms or a halogen atom.

In $R^2$, as the straight or branched alkyl group having 1 to 6 carbon atoms or the straight or branched alkoxy group having 1 to 6 carbon atoms, those mentioned in $R^1$ may be mentioned. In the formula (1), m is preferably an integer of 0 to 3, more preferably 0 or 1.

In $R^2$, the halogen atom may include a fluorine atom, a chlorine atom, a bromine atom and an iodine atom.

As the position of the alkyl group possessed by the monovalent monoalkylphenol is not specifically limited so long as it does not participate in the reaction. As these compounds, there may be mentioned, for example, o-, m- or p-cresol, o-, m- or p-ethylphenol, o-propylphenol, p-isopropylphenol, m-butylphenol, p-isobutylphenol, p-t-butylphenol, m-isobutylphenol, p-pentylphenol and p-hexyl-phenol.

As the halogen atom possessed by the monovalent halogenated phenol, fluorine, chlorine, bromine and iodine may be mentioned. A number and a position of the halogen atom are not specifically limited so long as it does not participate in the reaction. As these compounds, there may be mentioned, for example, o-, m- or p-fluorophenol, o-, m- or p-chlorophenol, o-, m- or p-bromophenol, o-, m- or p-iodophenol, 2,3-, 2,4-, 2,5-, 2,6-, 3,4- or 3,5-dichlorophenol, 2,3-, 2,4-, 2,5-, 2,6-, 3,4- or 3,5-dibromophenol, 2,3,4-, 2,3,5-, 2,3,6-, 2,4,5-, 2,4,6- or 3,4,5-trichlorophenol.

In the monovalent polyalkylphenol in which a plural number of alkyl groups as $R^2$ are substituted, a number and a position of the alkyl group are not specifically limited so long as they do not participate in the reaction. Such a compound may include, for example, 2,3-, 2,4-, 2,5-, 2,6-, 3,5- or 3,4-dimethylphenol, 2,3,4-, 2,3,5-, 2,3,6- or 3,4,5-trimethylphenol, 2,4,5-trimethylphenol, 2,3,4,5- or 2,3,5,6-tetramethylphenol, 2-ethyl-3-methylphenol, 3-t-butyl-4-methylphenol, 2-isopropyl-5-methylphenol, 2-pentyl-6-methylphenol and 3-hexyl-5-methylphenol.

In the monovalent polyalkylphenol in which a plural number of at least two of alkyl groups, alkoxy groups and halogen atoms as $R^2$ are substituted, a number and a position of the alkyl group, a number and a position of the alkoxy group and a number and a position of the halogen atom are not specifically limited so long as they do not participate in the reaction. Such a compound may include, for example, 2-methyl-3-fluorophenol, 2-methyl-3-chlorophenol, 2-methyl-3-bromophenol, 2-methyl-3-iodophenol, 2-methyl-4-fluorophenol, 2-methyl-4-chlorophenol, 2-methyl-4-bromophenol, 2-methyl-4-iodophenol, 4-chloro-2-isopropyl-5-methylphenol, 4-chloro-3,5-dimethylphenol, 4-bromo-2,6-dimethylphenol, 4-bromo-3,5-dimethylphenol, 2-methoxy-3-fluorophenol, 2-methoxy-3-chlorophenol, 2-methoxy-3-bromophenol, 2-methoxy-3-iodophenol, 2-methoxy-4-fluorophenol, 2-methoxy-4-chlorophenol, 2-methoxy-4-bromophenol, 2-methoxy-4-iodophenol, 4-chloro-2-isopropyl-5-methoxyphenol, 4-chloro-3,5-dimethoxyphenol, 4-bromo-2,6-dimethoxyphenol and 4-bromo-3,5-dimethoxyphenol.

As the ketone to be used in the process for preparing a dihydric phenol using the proton type β zeolite of the present invention, there may be mentioned, for example, a monoketone and a diketone. As the monoketone, a non-cyclic or cyclic monoketone may be mentioned. As the non-cyclic monoketone, for example, a straight or branched aliphatic monoketone having 3 to 20 carbon atoms, preferably 3 to 10 carbon atoms or an aromatic monoketone may be mentioned. The hydrogen atom(s) of these compounds may be substituted by a halogen atom(s) (a fluorine atom, a chlorine atom, a bromine atom or an iodine atom). A number and a position of the halogen atom are not specifically limited so long as they do not participate in the reaction.

As the straight aliphatic monoketone, there may be mentioned, for example, acetone, methyl ethyl ketone, 2-pentanone, 3-pentanone, 2-hexanone, 2-heptanone, 3-heptanone, 4-heptanone, 2-octanone, 2-nonanone, 3-decanone, 6-undecanone, 2-tridecanone, 7-tridecanone, 2-tetradecanone, 2-pentadecanone, 2-hexadecanone, 2-heptadecanone, 3-octadecanone, 4-nonadecanone, 1-chloro-2-propanone, 1-chloro-3-heptanone and 1-bromo-3-heptanone.

As the branched aliphatic monoketone, there may be mentioned, for example, 3-methyl-2-butanone, 3-methyl-2-pentanone, 4-methyl-2-pentanone, 3,3-dimethyl-2-butanone, 2,4-dimethyl-3-pentanone, 6-methyl-2-heptanone, 2,6-dimethyl-4-heptanone and 2,2,4,4-tetramethyl-3-heptanone. As the aromatic monoketone, there may be mentioned, for example, acetophenone, benzophenone, 1-phenyl-3-propanone, 1-phenyl-1-butanone, 1-phenyl-3-butanone, 1-phenyl-3-pentanone and 1,3-diphenyl-2-propanone.

As the cyclic monoketone, for example, a cycloalkyl monoketone having 5 to 12 carbon atoms may be mentioned. The hydrogen atom(s) of these compounds may be substituted by a substituent(s) such as a halogen atom (a fluorine atom, a chlorine atom, a bromine atom or an iodine atom), or a straight or branched alkyl group having 1 to 6 carbon atoms or the like. A number and a position of the substituent(s) are not specifically limited so long as they do not participate in the reaction. Such a compound may include, for example, cyclopentanone, cyclohexanone, cyclododecanone, 2-chlorocyclohexanone, 2-ethyl-1-cyclopentanone and 2-methyl-1-cyclohexanone.

As the diketone, a non-cyclic or a cyclic diketone may be mentioned. As the non-cyclic diketone, for example, a straight or branched aliphatic diketone having 5 to 21 carbon atoms, preferably 5 to 12 carbon atoms, or an aromatic diketone may be mentioned. A hydrogen atom(s) of these compounds may be substituted by a halogen atom (a fluorine atom, a chlorine atom, a bromine atom or an iodine atom). A number and a position of the halogen atom(s) are not specifically limited so long as they do not participate in the reaction. As the straight aliphatic diketone, for example, 2,3-butanedione, 2,4-pentanedione and 2,5-hexanedione may be mentioned. As the branched aliphatic diketone, for example, 2,5-dimethyl-3,4-hexanedione may be mentioned. As the aromatic diketone, for example, 1,2-diphenylethane-1,2-dione may be mentioned.

As the cyclic diketone, for example, a cyclic diketone having 5 to 12 carbon atoms may be mentioned. A hydrogen atom(s) of these compounds may be substituted by a substituent(s) such as a halogen atom (a fluorine atom, a chlorine atom, a bromine atom or an iodine atom), or a straight or branched alkyl group having 1 to 6 carbon atoms or the like. A number and a position of the substituent(s) are not specifically limited so long as they do not participate in the reaction. As the cyclic diketone, for example, 1,4-cyclohexanedione may be mentioned.

As the ketone preferably used in the process for preparing a dihydric phenol using the proton type β zeolite according to the present invention, a straight or branched aliphatic monoketone or a cyclic monoketone may be mentioned, more preferably a straight or branched aliphatic monoketone, and particularly preferably 4-methyl-2-pentanone or 3-pentanone.

An amount of the ketone to be used is preferably a ratio in which a molar ratio of the ketone based on an amount of the peroxide (ketone:peroxide) becomes 0.2:1 to 5:1.

To the process for preparing a dihydric phenol using the proton type β zeolite according to the present invention, a small amount of phosphoric acid may be added to avoid bad influence exerted to the reaction by a dissolved metal ion such as a small amount of iron ions, etc. whereas it is not necessarily essential. As the phosphoric acid, orthophosphoric acid, pyrophosphoric acid, metaphosphoric acid, triphosphoric acid, tetraphosphoric acid, polyphosphoric acid, phosphoric anhydride and an aqueous phosphoric acid solution may be mentioned, and an aqueous phosphoric acid solution is preferably used. A concentration of the aqueous phosphoric acid solution is preferably 0.001 to 100% by weight.

An amount of the phosphoric acid to be used is preferably a ratio in which a weigth ratio of the phosphoric acid based on an amount of the phenol (phosphoric acid: phenol) becomes 0.0001:1 to 0.05:1.

The peroxide to be used in the process for preparing a dihydric phenol using the proton type β zeolite according to the present invention may include an inorganic peroxide such as hydrogen peroxide, etc., or an organic peroxide such as ketone peroxide, aliphatic percarboxylic acid, etc.

As the ketone peroxide, for example, a dialkylketone peroxide preferably having 3 to 20 carbon atoms, more preferably 3 to 10 carbon atoms may be preferably mentioned. As these compounds, there may be mentioned, for example, dimethyl ketone peroxide, diethyl ketone peroxide, methyl ethyl ketone peroxide, methyl-n-propyl ketone peroxide, methyl isopropyl ketone peroxide, methyl isobutyl ketone peroxide and the like.

As the aliphatic percarboxylic acid, peracetic acid, perpropionic acid, etc. may be mentioned.

As the hydrogen peroxide, an aqueous hydrogen peroxide with a concentration of 0.1% by weight or more, preferably 0.1 to 90% by weight may be used, and that with 30 to 80% by weight is further preferably used.

As the peroxide to be used in the process for preparing a dihydric phenol using the proton type β zeolite according to the present invention, hydrogen peroxide or a ketone peroxide is preferably used. This ketone peroxide can be synthesized by contacting a ketone and hydrogen peroxide, and the ketone to be used here is the same as those mentioned above.

An amount of the peroxide to be used is preferably in a range in which a molar ratio of the peroxide to the amount of the phenol (peroxide:phenol) becomes 1:1 to 1:100, more preferably in the range of 1:5 to 1:20.

Next, in the formula (1), when $R^1$ is a straight or branched alkyl group having 1 to 6 carbon atoms or a straight or branched alkoxy group having 1 to 6 carbon atoms, and $R^2$ is a hydrogen atom, a straight or branched alkyl group having 1 to 6 carbon atoms or a halogen atom, the process becomes a reaction in which the substituted benzene compound is oxidized to obtain a substituted phenol compound. In the present invention, to prepare a para position substituted phenol compound predominantly, the benzene compound represented by the formula (1) is oxidized by a peroxide in the presence of the above-mentioned proton type P zeolite, ketone and phosphoric acid whereby the object can be accomplished. Also, to prepare an ortho position substituted phenol compound predominantly, the benzene compound represented by the formula (1) is oxidized by a peroxide in the presence of the above-mentioned proton type β zeolite, carboxylic acid and phosphoric acid whereby the object can be accomplished.

In the above-mentioned formula (1), when $R^1$ is a stranght or branched alkyl group having 1 to 6 carbon atoms or a straight or branched alkoxy group having 1 to 6 carbon atoms, it is preferred that n=1 and $R^2$ are all hydrogen atoms.

As the preferred embodiments for the above-mentioned benzene compound, there may be mentioned a benzene compound substituted by an alkyl group, a benzene compound substituted by an alkyl group and a halogen atom, a benzene compound substituted by an alkoxy group, a benzene compound substituted by an alkoxy group and a halogen atom and the like. As the benzene compound substituted by an alkyl group, there may be mentioned, for example, methylbenzene, ethylbenzene, n-propylbenzene, isopropylbenzene, n-butylbenzene, t-butylbenzene, o-, m- or p-xylene, 1,2,3-, 1,2,4- or 1,3,5-trimethylbenzene, 1,2,3,4-, 1,2,3,5- or 1,2,4,5-tetramethylbenzene, etc. As the benzene compound substituted by an alkyl group and a halogen atom, there may be mentioned, for example, 2-chlorotoluene, 3-chlorotoluene, 4-chlorotoluene, 2-fluorotoluene, 3-fluorotoluene, 4-fluorotoluene, 2-bromotoluene, 3-bromotoluene, 4-bromotoluene, etc.

As the benzene compound substituted by an alkoxy group, there may be mentioned, for example, methoxybenzene (anisole), ethoxybenzene, n-propoxy benzene, isopropoxy benzene, n-butoxy benzene, t-butoxy benzene, o-, m- or p-dimethoxybenzene, 1,2,3-, 1,2,4- or 1,3,5-trimethoxybenzene, 1,2,3,4-, 1,2,3,5- or 1,2,4,5-tetramethoxybenzene, etc. As the benzene compound substituted by an alkoxy group and a halogen atom, there may be mentioned, for example, 2-chloroanisole, 3-chloroanisole, 4-chloroanisole, 2-fluoroanisole, 3-fluoroanisole, 4-fluoroanisole, 2-bromoanisole, 3-bromoanisole, 4-bromoanisole, etc.

In the compound represented by the above-mentioned formula (2), $R^3$ is the same as $R^2$ as mentioned above. q is preferably 0 to 2, more preferably 0 or 1.

Also, as the compound represented by the above-mentioned formula (2), 1,2-methylenedioxybenzene (1,3-benzodioxole), 3-methyl-1,2-methylenedioxybenzene, 3-chloro-1,2-methylenedioxybenzene, etc. when p is 1, and 1,2-ethylenedioxybenzene (1,4-benzodioxole), 3-methyl-1,2-ethylenedioxybenzene, 3-chloro-1,2-ethylenedioxybenzene, etc. when p is 2 are mentioned.

As the ketone to be used for predominantly preparing a para-position substituted phenol compound in the present invention, the above-mentioned ketones may be mentioned.

As the ketone to be preferably used in the present invention, a straight or branched aliphatic monoketone, or a cyclic monoketone may be mentioned, further preferably a straight or branched aliphatic monoketone, and of these, 3,3-dimethyl-2-butanone (in the following, it is described as "pinacolin" which is common name), 4-methyl-2-pentanone, 3-pentanone, and 3,3-dimethyl-2-butanone is particularly preferred.

An amount of the ketone to be used, a kind and an amount of the phosphoric acid to be used, a kind and an amount of the peroxide to be used, a method of adding the peroxide to the reaction system are the same as those mentioned above.

In the above-mentioned preparation process, the proton type β zeolite of the present invention, or at least one metal selected from the group consisting of an alkaline earth metal (Be, Mg, Ca, Sr, Ba), a transition metal (Fe, Co, Ni, Ru, Rh, Pd, Os, Ir, Pt), Group 2B metals (Zn, Cd, Hg), Group 3A metals (Al, Ga, In, Tl), Group 4A metal (Sn, Pb) of the Periodic Table, or a lanthanide metal (from Ce to Lu), etc. is carried on the above zeolite may be used.

As the carboxylic acid to be used for predominantly preparing an ortho-position substituted phenol compound in the present invention, for example, a monocarboxylic acid and a dicarboxylic acid may be mentioned. As the monocarboxylic acid, for example, a straight or branched aliphatic monocarboxylic acid having 1 to 20 carbon atoms, preferably 1 to 10 carbon atoms, and an aromatic monocarboxylic acid may be mentioned. The hydrogen atom(s) of these compounds may be substituted by a halogen atom(s) (fluorine, chlorine, bromine or iodine). A number and a position of the halogen atom(s) are not specifically limited so long as they do not participate in the reaction.

As the straight aliphatic monocarboxylic acid, there may be mentioned, for example, formic acid, acetic acid, monochloroacetic acid, dichloroacetic acid, trichloroacetic acid, monofluoroacetic acid, difluoroacetic acid, trifluoroacetic acid, bromoacetic acid, propanoic acid, butanoic acid, pentanoic acid, hexanoic acid, heptanoic acid, octanoic acid, nonanoic acid and decanoic acid.

As the branched aliphatic monocarboxylic acid, there may be mentioned, for example, 2-methylpropanoic acid, 2-fluoropropanoic acid, 2-chloropropanoic acid, 2-bromopropanoic acid, 2,2-dimethylpropanoic acid, 2-methylbutanoic acid, 2,2-dimethylbutanoic acid, 3-methylbutanoic acid, 2,3-dimethylbutanoic acid and 3,3-dimethylbutanoic acid. As the aromatic monocarboxylic acid, for example, benzoic acid and phenylacetic acid may be mentioned.

As the dicarboxylic acid, for example, a straight or branched aliphatic dicarboxylic acid having 2 to 20 carbon atoms, preferably 2 to 10 carbon atoms, or an aromatic dicarboxylic acid may be mentioned. The hydrogen atom(s) of these compounds may be substituted by a halogen atom(s) (fluorine, chlorine, bromine or iodine). A number and a position of the halogen atom(s) are not specifically limited so long as they do not participate in the reaction. As the straight aliphatic dicarboxylic acid, there may be mentioned, for example, oxalic acid, acetic anhydride, 1,3-propanedicarboxylic acid, 1,4-butanedicarboxylic acid, 1,5-pentanedicarboxylic acid, 1,6-hexanedicarboxylic acid, fumaric acid, maleic acid and maleic anhydride. As the branched aliphatic dicarboxylic acid, for example, 2-methyl-1,3-propanedicarboxylic acid and 2,2-dimethyl-1,3-propanedicarboxylic acid may be mentioned. As the aromatic dicarboxylic acid, for example, phthalic acid may be mentioned.

As the carboxylic acid to be preferably used in the present invention, a straight aliphatic monocarboxylic acid having 1 to 10 carbon atoms may be mentioned, and of these, acetic acid and propanoic acid are particularly preferred.

An amount of the carboxylic acid to be used is preferably a ratio in which a molar ratio of the carboxylic acid to the amount of the peroxide (carboxylic acid:peroxide) becomes 0.2:1 to 5:1.

A kind and an amount of the phosphoric acid to be used are the same as those mentioned above.

As the peroxide to be used for predominantly preparing an ortho-position substituted phenol compound in the present invention, an inorganic peroxide such as hydrogen peroxide, etc., or a carboxylic acid peroxide may be mentioned.

As the carboxylic acid peroxide, for example, those having 2 to 20 carbon atoms, preferably those having 2 to 10 carbon atoms may be mentioned. As these compounds, there may be mentioned, for example, acetic acid peroxide, propanoic acid peroxide, butanoic acid peroxide, 2-methylpropanoic acid peroxide, 2-fluoropropanoic acid peroxide, 2-chloropropanoic acid peroxide, 2-bromopropanoic acid peroxide, 2,2-dimethylpropanoic acid peroxide, 2-methylbutanoic acid peroxide, 2,2-dimethylbutanoic acid peroxide, 3-methylbutanoic acid peroxide, 2,3-dimethylbutanoic acid peroxide, 3,3-dimethylbutanoic acid peroxide and the like.

As the hydrogen peroxide, 0.1% by weight or more, preferably 0.1 to 90% by weight aqueous hydrogen peroxide can be used, and 30 to 80% by weight one is more preferably used.

As the peroxide to be used for predominantly preparing an ortho-position substituted phenol compound in the present invention, aqueous hydrogen peroxide or a carboxylic acid peroxide having 2 to 10 carbon atoms is preferably used, and 30 to 80% by weight aqueous hydrogen peroxide, an acetic acid peroxide, or a propanoic acid peroxide are more preferably used. The carboxylic acid peroxide can be synthesized by contacting a carboxylic acid and hydrogen peroxide, and the carboxylic acid herein used is the same as those mentioned above.

An amount of the peroxide to be used and a method of adding the peroxide to the reaction system are the same as those mentioned above.

The acidic zeolite to be used for predominantly preparing an ortho-position substituted phenol compound in the present invention, a proton type material of various kinds of zeolites such as X, Y, ZSM-5, ZSM-11, mordenite, chabazite, β, etc., preferably used is the above-mentioned proton type β zeolite of the present invention.

As a method of adding the peroxide to the reaction system, a whole amount thereof may be added at the time of initiating the reaction, and to prevent from occurrence of a side reaction and to proceed the reaction with high yield, it is preferred to add the peroxide by dividing into several times or a small amount of the same is continuously added by using a liquid feeding pump such as a plunger pump. When the peroxide is added by dividing into several portions, an amount of the peroxide based on the amount of the benzene compound per one time is preferably 0.05:100 to 2:100, more preferably 0.1:100 to 2:100 in terms of a molar ratio (peroxide:benzene compound). Also, in either of the divisional addition or the continuous addition, an amount of the peroxide in the reaction system based on the amount of the benzene compound is preferably in the range of 0.05:100 to 2:100, more preferably 0.1:100 to 1:100 in terms of a molar ratio.

As a shape of the proton type β zeolite of the present invention to be used for preparing the above-mentioned phenol compound, powder, granule, extrudates, honeycomb shaped molded material, etc., may be mentioned.

As a shape in accordance with the preparation of the above-mentioned phenol compound, for example, powder, granule, etc. are preferably used when a liquid phase batch system reactor is used for preparation, and pellet, honeycomb shaped molded material, etc. are preferably used when a liquid phase flow system reactor is used for preparation.

In the preparation of the above-mentioned phenol compound, an amount of the proton type β zeolite to be used based on the amount of the benzene compound is preferably in the range of 1:1 to 1:500, more preferably in the range of 1:5 to 1:100 in terms of a weight ratio of the proton type β zeolite to the benzene compound (β zeolite:benzene compound).

A reaction temperature in the preparation of the above-mentioned phenol compound is preferably 20 to 300° C., more preferably 40 to 200° C. A reaction time may vary depending on, for example, the difference in Al:Si (atomic ratio) of the proton type β zeolite or the reaction temperature, but not specifically limited. Also, the reaction can be carried out under atmospheric pressure but may be carried out under reduced pressure or under pressure. The reaction can be carried out in a liquid phase by a batch system, a flow system, a trickle bed system, etc.

As a method for preparing the above-mentioned phenol compound, there may be mentioned a method, for example, in which a benzene compound, hydrogen peroxide, a ketone and/or a carboxylic acid and phosphoric acid are fed to a reactor in which the proton type β zeolite has previously been filled, to oxidize the benzene compound to form a phenol compound, and a reaction mixture is exhausted from the reactor, and the like.

The phenol compound obtained by the above-mentioned preparation process of the phenol compound can be obtained as a single compound or a mixture of several kinds depending on the structure of the benzene compound(s) to be used as a starting material(s). Also, these phenol compounds can be obtained by separating and purifying according to the conventional manner.

EXAMPLES

In the following, the present invention is specifically explained by referring to Examples and Comparative examples. Incidentally, the present invention is not limited by these Examples.

A yield of the dihydric phenol was obtained in accordance with the following equation. Incidentally, analysis was carried out by gas chromatography.

Yield of dihydric phenol (%)={(molar number of formed dihydric phenol)÷(molar number of charged peroxide)}×100

Example 1

Preparation of H/β HNO₃ (38)

In 40 ml of eggplant flask into which an aqueous nitric acid solution (pH=1.35) had been charged was charged 5.0 g of the proton type β zeolite powder with Al:Si=1:38 (hereinafter referred to as H/β (38)) available from ZEOLYST INTERNATIONAL, the mixture was heated to 80° C. by an oil bath and stirred. After 2 hours, zeolite was removed by filtration, the filtrate was washed with deionized water, dried at 110° C., and calcined at 550° C. in air for 2.5 hous. When the resulting proton type β zeolite (hereinafter referred to as H/β HNO₃ (38)) was analyzed by ICP atomic emission spectroanalysis, then Al:Si (atomic ratio) of the β zeolite was Al:Si=1:78. Also, when the NH₃-TPD measurement (Temperature raising rate: 20° C./minute, Measured range: 100° C. to 700° C.) was carried out, the desorption peak belonging to the strong acid site at 500° C. or higher was markedly lowered (see FIG. 2) as compared to that no treatment was carried out. From the NH₃-TPD spectrum shown in this figure, when an amount of the strong acid site existing in a temperature region of 500° C. or higher was calculated from the above-mentioned equation 1, it was 0.55 μmol/g, whereas that no nitric acid treatment was carried out (H/β (38)) was 3.0 mmol/g whereby remarkable difference was admitted. Also, when FT-IR spectrum was compared, no absorption at 3782 cm$^{-1}$ which had been detected in H/β (38) was detected (see FIG. 3).

Example 2

Preparation of H/β HNO₃ (13)

In 40 ml of an eggplant flask into which an aqueous nitric acid solution (pH=1.30) had been charged was charged 5.0 g of the proton type β zeolite powder with Al:Si=1:13

(hereinafter referred to as H/β (13)) available from ZEOLYST INTERNATIONAL, and the mixture was heated to 80° C. by an oil bath and stirred. After 2 hours, zeolite was removed by filtration, and the filtrate was washed with deionized water, dried at 110° C., and calcined at 550° C. in air for 2.5 hours. When the resulting proton type β zeolite (hereinafter referred to as H/β HNO$_3$ (13)) was analyzed by ICP atomic emission spectroanalysis, Al:Si (atomic ratio) in the β zeolite was Al:Si=1:69. Also, when the NH$_3$-TPD measurement (Temperature raising rate: 20° C./minute, Measured range: 100° C. to 700° C.) was carried out, a desorption peak belonging to the strong acid site of 500° C. or higher is markedly lowered as compared to those of untreated one (H/β (13)). An amount of the strong acid site calculated in the same manner as in Example 1 was 1.8 mmol/g in H/p HNO$_3$ (13), whereas it was 4.2 mmol/g in H/β (13), whereby remarkable difference was admitted.

Also, when the FT-IR spectra were compared to each other, an absorption at 3782 cm$^{-1}$ detected in H/β (13) was not detected.

Example 3

In 300 ml of flask were charged 0.20 g of H/β HNO$_3$ (38) prepared in Example 1, 10.0 g of phenol, 0.27 g of 3-pentanone and 0.02 g of a 85% by weight aqueous phosphoric acid solution, and after the atmosphere was replaced with nitrogen, the temperature of the mixture was raised to 60° C. under stirring. Then, at the same temperature, 0.10 g of a 60% by weight aqueous hydrogen peroxide was added dropwise to the mixture, further added dropwise 0.10 g of the same after 1.5 minutes, and 0.10 g after 3 minutes, and the reaction was carried out for 5 minutes from the initial dropwise addition.

As a result, yield of the dihydric phenol was 52.8% of catechol and 41.5% of hydroquinone, and the total yield of the catechol and the hydroquinone was 94.3%.

Example 4

Reaction was carried out in the same manner as in Example 3 except for changing the reaction temperature to 100° C.

As a result, yield of the dihydric phenol was 54.9% of catechol and 41.1% of hydroquinone, and the total yield of the catechol and the hydroquinone was 96.0%.

Comparative Example 1

The same reaction was carried out as in Example 3 except for changing H/β HNO$_3$ (38) to H/β (38).

As a result, yield of the dihydric phenol was 50.0% of catechol and 34.7% of hydroquinone, and the total yield of the catechol and the hydroquinone was 84.7%.

Comparative Example 2

The same reaction was carried out as in Comparative example 1 except for seting the reaction temperature to 100° C.

As a result, yield of the dihydric phenol was 51.4% of catechol and 33.6% of hydroquinone, and the total yield of the catechol and the hydroquinone was 85.0%.

Example 5

The same reaction was carried out as in Example 4 except for changing H/β HNO$_3$ (38) to H/β HNO$_3$ (13).

As a result, yield of the dihydric phenol was 52.6% of catechol and 39.1% of hydroquinone, and the total yield of the catechol and the hydroquinone was 91.7%.

Comparative Example 3

The same reaction was carried out as in Example 4 except for changing H/β HNO$_3$ (38) to H/β (13).

As a result, yield of the dihydric phenol was 49.3% of catechol and 33.8% of hydroquinone, and the total yield of the catechol and the hydroquinone was 83.1%.

TABLE 1

| | Proton type β zeolite | Reaction temperature (° C.) | Amount of strong acid site (μmol/g) | Yield of dihydric phenol (%) |
|---|---|---|---|---|
| Example 3 | H/β HNO$_3$ (38) | 60 | 0.55 | 94.3 |
| Example 4 | H/β HNO$_3$ (38) | 100 | 0.55 | 96.0 |
| Comparative example 1 | H/β (38) | 60 | 3.0 | 84.7 |
| Comparative example 2 | H/β (38) | 100 | 3.0 | 85.0 |
| Example 5 | H/β HNO$_3$ (13) | 100 | 1.8 | 91.7 |
| Comparative example 3 | H/β (13) | 100 | 4.2 | 83.1 |

Note)
H/β HNO$_3$ (38); Proton type β zeolite with Al:Si = 1:38 was treated by nitric acid
H/β (38); Proton type β zeolite with Al:Si = 1:38
H/β HNO$_3$ (13); Proton type β zeolite with Al:Si = 1:13 was treated by nitric acid
H/β (13); Proton type β zeolite with Al:Si = 1:13

Example 6

In 300 ml of flask were charged 0.20 g of H/β HNO$_3$ (38) prepared in Example 1, 10.0 g of phenol and 0.27 g of 3-pentanone, and after the atmosphere was replaced with nitrogen, the temperature of the mixture was raised to 100° C. under stirring. Then, at the same temperature, 0.10 g of a 60% by weight aqueous hydrogen peroxide was added dropwise to the mixture, further added dropwise 0.10 g of the same after 1.5 minutes, 0.10 g after 3 minutes, 0.1 g after 4.5 minutes, 0.1 g after 6 minutes and 0.1 g after 7.5 minutes, and the reaction was carried out for 10 minutes from the initial dropwise addition.

As a result, yield of the dihydric phenol was 48.4% of catechol and 43.7% of hydroquinone, and the total yield of the catechol and the hydroquinone was 92.1%.

Example 7

The same reaction was carried out as in Example 6 except for adding 0.02 g of a 85% aqueous phosphoric acid solution to the starting materials before the reaction.

As a result, yield of the dihydric phenol was 50.4% of catechol and 40.4% of hydroquinone, and the total yield of the catechol and the hydroquinone was 90.8%.

Comparative Example 4

The same reaction was carried out as in Example 6 except for changing H/β HNO₃ (38) to H/β (38).

As a result, yield of the dihydric phenol was 45.1% of catechol and 38.0% of hydroquinone, and the total yield of the catechol and the hydroquinone was 83.1%.

Comparative Example 5

The same reaction was carried out as in Example 7 except for changing H/β HNO₃ (38) to H/β (38).

As a result, yield of the dihydric phenol was 47.7% of catechol and 33.0% of hydroquinone, and the total yield of the catechol and the hydroquinone was 80.7%.

TABLE 2

|   | Proton type β zeolite | Amount of strong acid site (μmol/g) | Addition of phosphoric acid | Yield of dihydric phenol (%) |
|---|---|---|---|---|
| Example 6 | H/β HNO₃ (38) | 0.55 | None | 92.1 |
| Example 7 | H/β HNO₃ (38) | 0.55 | Done | 90.8 |
| Comparative example 4 | H/β (38) | 3.0 | None | 83.1 |
| Comparative example 5 | H/β (38) | 3.0 | Done | 80.7 |

Note)
H/β HNO₃ (38); Proton type β zeolite with Al:Si = 1:38 was treated by nitric acid
H/β (38); Proton type β zeolite with Al:Si = 1:38

Reference Example 1

Preparation of Calcium-Carried Proton Type β Zeolite

A Ca ion-containing aqueous solution in an amount of 15 ml was prepared by dissolving 1.8 g of calcium nitrate tetrahydrate in deionized water. In the resulting aqueous solution was immersed 2 g of the proton type β zeolite prepared in Example 1, and the mixture was maintained at 85° C. for 14 hours to carry out ion-exchange of a proton to a calcium ion. The obtained suspension was subjected to suction filtration, dried at 110° C., and then, calcined at 550° C. for 2.5 hours to obtain 1.9 g of a calcium-carried proton type β zeolite (hereinafter referred to as "Ca/H/P HNO₃").

When ICP atomic emission spectroanalysis was carried out with regard to Ca/H/β HNO₃ as mentioned above, a ratio of calcium and Al (atomic ratio) introduced in said β zeolite was Ca/Al=0.41.

Example 8

In 300 ml of a flask were charged 0.50 g of H/β HNO₃ prepared in Example 1, 46.0 g (0.425 mol) of anisole, 1.06 g (0.0106 mol) of pinacolin (3,3-dimethyl-2-butanone) and 0.02 g of a 85% by weight aqueous phosphoric acid solution, and after the atmosphere was replaced with nitrogen, the temperature of the mixture was raised to 120° C. by an oil bath under stirring. Then, at the same temperature, 0.10 g of a 60% by weight aqueous hydrogen peroxide was added dropwise to the mixture, and further added dropwise each 0.10 g of the same with an interval of after 3 minutes, 6 minutes, 9 minutes, 12 minutes and 15 minutes, whereby 0.60 g (0.0106 mol) in total was added to the mixture by dividing aqueous hydrogen peroxide into six portions. The reaction was carried out for 60 minutes from the initial dropwise addition.

As a result, yield of the methoxyphenol was 35.8% of o-methoxyphenol and 52.2% of p-methoxyphenol, and the total yield was 88.0%. The reaction mixture was slightly colored to a pale red color, and accumulation of tar components was substantially not observed.

Example 9

The same reaction was carried out as in Example 8 except for using Ca/H/β HNO₃ prepared in Reference example 1 as a catalyst.

As a result, yield of the methoxyphenol was 35.0% of o-methoxyphenol and 50.2% of p-methoxyphenol, and the total yield was 85.2%. The reaction mixture was slightly colored to a pale red color, and accumulation of tar components was substantially not observed.

Comparative Example 6

The same reaction was carried out as in Example 8 except for using 0.02 g of 98% conc. sulfuric acid as a catalyst.

As a result, yield of the methoxyphenol was 21.6% of o-methoxyphenol and 3.8% of p-methoxyphenol, and the total yield was 25.4%. The reaction mixture was colored to a red brown color, and accumulation of tar components was observed.

Comparative Example 7

The same reaction was carried out as in Example 8 except for changing the catalyst to US-Y with Al:Si=1:3.0 available from NIKKI-UNIVERSAL CO., LTD. as a catalyst.

As a result, yield of the methoxyphenol was 34.9% of o-methoxyphenol and 12.2% of p-methoxyphenol, and the total yield was 47.1%. The reaction mixture was slightly colored to a pale red color, and accumulation of tar components was substantially not observed.

Comparative Example 8

The same reaction was carried out as in Example 8 except for changing the catalyst to TS-1 with Ti:Si=1:38.0 available from N.E.CHEMCAT CORPORATION as a catalyst, and omitting pinacolin and phosphoric acid.

As a result, yield of the methoxyphenol was 4.2% of o-methoxyphenol and 14.9% of p-methoxyphenol, and the total yield was 19.1%. The reaction mixture was slightly colored to a pale red color, and accumulation of tar components was substantially not observed.

TABLE 3

|   | Catalyst | Ketone | Yield of methoxyphenol (%) | o/p ratio |
|---|---|---|---|---|
| Example 8 | H/β HNO₃ | Pinacolin | 88.0 | 0.69 |
| Example 9 | Ca/H/β HNO₃ | Pinacolin | 85.2 | 0.70 |
| Comparative example 6 | H₂SO₄ | Pinacolin | 25.4 | 5.68 |

TABLE 3-continued

| | Catalyst | Ketone | Yield of methoxyphenol (%) | o/p ratio |
|---|---|---|---|---|
| Comparative example 7 | US-Y | Pinacolin | 47.1 | 2.86 |
| Comparative example 8 | TS-1 | — | 19.1 | 0.28 |

H/β HNO$_3$: Proton type β zeolite treated with an aqueous nitric acid solution
Ca/H/β HNO$_3$: Proton type β zeolite carrying calcium thereon and treated with an aqueous nitric acid solution
o/p ratio: A formation ratio of the ortho-position substituted material/the para-position substituted material Example 10

In 300 ml of a flask were charged 0.20 g of the proton type β zeolite treated with nitric acid and prepared in Example 1, 11.5 g (0.106 mol) of anisole, 0.27 g (0.00321 mol) of diethylketone and 0.02 g of a 85% by weight aqueous phosphoric acid solution, and after the atmosphere was replaced with nitrogen, the temperature of the mixture was raised to 120° C. by an oil bath under stirring. Then, at the same temperature, 0.10 g of a 60% by weight aqueous hydrogen peroxide was added dropwise to the mixture, further added dropwise 0.10 g of the same after 3 minutes and 0.10 g after 6 minutes whereby 0.30 g (0.00529 mol) in total was added to the mixture by dividing into three portions. After 10 minutes, a temperature of the oil bath was raized to 140° C., and the reaction was carried out for 60 minutes from the initial dropwise addition.

As a result, yield of the methoxyphenol was 32.6% of o-methoxyphenol and 44.4% of p-methoxyphenol, and the total yield was 77.0%. The reaction mixture was slightly colored to a pale red brown color, and accumulation of tar components was substantially not observed.

Example 11

The same reaction was carried out as in Example 10 except for changing ketone to 0.63 g (0.00629 mol) of methyl isobutyl ketone (4-methyl-2-pentanone).

As a result, yield of the methoxyphenol was 34.6% of o-methoxyphenol and 37.9% of p-methoxyphenol, and the total yield was 72.5%. The reaction mixture was slightly colored to a pale red brown color, and accumulation of tar components was substantially not observed.

Example 12

The same reaction was carried out as in Example 10 except for changing ketone to 0.32 g (0.00319 mol) of pinacolin (3,3-dimethyl-2-butanone).

As a result, yield of the methoxyphenol was 33.5% of o-methoxyphenol and 46.4% of p-methoxyphenol, and the total yield was 79.9%. The reaction mixture was slightly colored to a pale red brown color, and accumulation of tar components was substantially not observed.

TABLE 4

| | Catalyst | Ketone | Yield of methoxyphenol (%) | o/p ratio |
|---|---|---|---|---|
| Example 10 | H/β HNO$_3$ | Diethyl ketone | 77.0 | 0.73 |
| Example 11 | H/β HNO$_3$ | Methyl isobutyl ketone | 72.5 | 0.91 |
| Example 12 | H/β HNO$_3$ | Pinacolin | 79.9 | 0.72 |

H/β HNO$_3$: Proton type β zeolite treated with an aqueous nitric acid solution

Example 13

The same reaction was carried out as in Example 8 except for using 52.0 g (0.425 mol) of phenetol (ethoxybenzene) as a reaction substrate in place of anisole.

As a result, yield of the methoxyphenol was 32.5% of o-methoxyphenol and 46.1% of p-methoxyphenol, and the total yield was 78.6%. The reaction mixture was slightly colored to a pale red color, and accumulation of tar components was substantially not observed.

TABLE 5

| | Catalyst | Reaction substrate | Ketone | Yield of ethoxyphenol (%) | o/p ratio |
|---|---|---|---|---|---|
| Example 13 | H/β HNO$_3$ | Phenetol | Pinacolin | 78.6 | 0.71 |

H/β HNO$_3$: Proton type β zeolite treated with an aqueous nitric acid solution

Example 14

In 300 ml of a flask were charged 0.50 g of H/β HNO$_3$ prepared in Example 1, 46.0 g (0.425 mol) of anisole, 0.64 g (0.0107 mol) of acetic acid and 0.02 g of a 85% by weight aqueous phosphoric acid solution, and after the atmosphere was replaced with nitrogen, the temperature of the mixture was raised to 100° C. by an oil bath under stirring. Then, at the same temperature, 0.10 g of a 60% by weight aqueous hydrogen peroxide was added dropwise to the mixture, and further added dropwise each 0.10 g of the same with an interval of after 3 minutes, 6 minutes, 9 minutes, 12 minutes and 15 minutes, whereby 0.60 g (0.0106 mol) in total was added to the mixture by dividing the aqueous hydrogen peroxide into six portions. The reaction was carried out for 180 minutes from the initial dropwise addition.

As a result, yield of the methoxyphenol was 48.5% of o-methoxyphenol and 29.3% of p-methoxyphenol, and the total yield was 77.8%. The reaction mixture was slightly colored to a pale red color, and accumulation of tar components was substantially not observed.

Example 15

In 300 ml of a flask were charged 0.20 g of Ca/H/β HNO$_3$ prepared in Reference example 1, 23.0 g (0.213 mol) of anisole, 0.32 g (0.00535 mol) of acetic acid and 0.02 g of a 85% by weight aqueous phosphoric acid solution, and after the atmosphere was replaced with nitrogen, the temperature of the mixture was raised to 100° C. by an oil bath under stirring. Then, at the same temperature, 0.10 g of a 60% by weight aqueous hydrogen peroxide was added dropwise to the mixture, further added dropwise each 0.10 g of the same after 3 minutes and 6 minutes, whereby 0.30 g (0.00530 mol) in total was added to the mixture by dividing the aqueous hydrogen peroxide into three portions. The reaction was carried out for 180 minutes from the initial dropwise addition.

As a result, yield of the methoxyphenol was 49.5% of o-methoxyphenol and 29.9% of p-methoxyphenol, and the total yield was 79.4%. The reaction mixture was slightly colored to a pale red color, and accumulation of tar components was substantially not observed.

Comparative Example 9

The same reaction was carried out as in Example 14 except for changing the catalyst to H/β (38) and for not adding acetic acid.

As a result, yield of the methoxyphenol was 28.0% of o-methoxyphenol and 12.4% of p-methoxyphenol, and the total yield was 40.4%.

TABLE 6

| | Catalyst | Carboxylic acid | Yield of methoxyphenol (%) | o/p ratio |
|---|---|---|---|---|
| Example 14 | H/β HNO$_3$ | Acetic acid | 77.8 | 1.66 |
| Example 15 | Ca/H/β HNO$_3$ | Acetic acid | 79.4 | 1.66 |
| Comparative example 9 | H/β | — | 40.4 | 2.25 |

H/β HNO$_3$: Proton type β zeolite treated with aqueous nitric acid solution
Ca/H/β HNO$_3$: Proton type β zeolite carrying calcium thereon and treated with aqueous nitric acid solution
H/β: Proton type β zeolite
o/p ratio: A formation ratio of the ortho-position substituted material/the para-position substituted material Example 16

In 300 ml of a flask were charged 0.20 g of H/β HNO$_3$ prepared in Example 1, 11.5 g (0.106 mol) of anisole, 0.20 g (0.00333 mol) of acetic acid and 0.02 g of a 85% by weight aqueous phosphoric acid solution, and after the atmosphere was replaced with nitrogen, the temperature of the mixture was raised to 120° C. by an oil bath under stirring. Then, at the same temperature, 0.10 g of a 60% by weight aqueous hydrogen peroxide was added dropwise to the mixture, further added dropwise each 0.10 g of the same after 3 minutes and 6 minutes whereby 0.30 g (0.00529 mol). in total was added to the mixture by dividing the aqueous hydrogen peroxide into three portions. After 10 minutes, a temperature of the oil bath was raized to 140° C., and the reaction was carried out for 60 minutes from the initial dropwise addition.

As a result, yield of the methoxyphenol was 39.9% of o-methoxyphenol and 28.5% of p-methoxyphenol, and the total yield was 68.4%.

Example 17

The same reaction was carried out as in Example 16 except for changing the carboxylic acid to 0.24 g (0.00324 mol) of propanoic acid (propionic acid).

As a result, yield of the methoxyphenol was 34.2% of o-methoxyphenol and 23.7% of p-methoxyphenol, and the total yield was 57.9%.

Example 18

The same reaction was carried out as in Example 16 except for changing the carboxylic acid to 0.28 g (0.00318 mol) of 2-methylpropanoic acid (isobutyric acid).

As a result, yield of the methoxyphenol was 28.8% of o-methoxyphenol and 21.3% of p-methoxyphenol, and the total yield was 50.1%.

Example 19

The same reaction was carried out as in Example 16 except for changing the carboxylic acid to 0.33 g (0.00323 mol) of 2,2-dimethylpropanoic acid (pivalic acid).

As a result, yield of the methoxyphenol was 27.7% of o-methoxyphenol and 22.1% of p-methoxyphenol, and the total yield was 49.8%.

TABLE 7

| | Catalyst | Carboxylic acid | Yield of methoxyphenol (%) | o/p ratio |
|---|---|---|---|---|
| Example 16 | H/β HNO$_3$ | Acetic acid | 68.4 | 1.40 |
| Example 17 | H/β HNO$_3$ | Propionic acid | 57.9 | 1.44 |
| Example 18 | H/β HNO$_3$ | Isobutyric acid | 50.1 | 1.35 |
| Example 19 | H/β HNO$_3$ | Pyvalic acid | 49.8 | 1.25 |

H/β HNO$_3$: Proton type β zeolite treated with an aqueous nitric acid solution

Example 20

The same reaction was carried out as in Example 14 except that 52.0 g (0.425 mol) of phenetol (ethoxybenzene) was used as a reaction substrate in place of anisole, the reaction temperature was set to 120° C., and the reaction time was set to 60 minutes.

As a result, yield of the ethoxyphenol was 44.3% of o-ethoxyphenol and 29.9% of p-ethoxyphenol, and the total yield was 74.2%. The reaction mixture was slightly colored to red color, and accumulation of tar components was substantially not observed.

TABLE 8

| | Catalyst | Reaction substrate | Carboxylic acid | Yield of ethoxyphenol (%) | o/p ratio |
|---|---|---|---|---|---|
| Example 20 | H/β HNO$_3$ | Phenethol | Acetic acid | 74.2 | 1.48 |

H/β HNO$_3$: Proton type β zeolite treated with an aqueous nitric acid solution

Example 21

In 300 ml of a flask were charged 0.20 g of H/β HNO$_3$ (38) prepared in Example 1, 9.80 g of toluene, 0.27 g of 3-pentanone and 0.02 g of a 85% by weight aqueous phosphoric acid solution, and after the atmosphere was replaced with nitrogen, the temperature of the mixture was raised to 120° C. under stirring. Then, at the same temperature, 0.10 g of a 60% by weight aqueous hydrogen peroxide was added dropwise to the mixture, further added dropwise 0.10 g of the same after 1.5 minutes and 0.10 g after 3 minutes, and the reaction was carried out for 60 minutes from the initial dropwise addition.

As a result, yield of o-cresol which is an oxidized product of toluene was 16.2%, and p-cresol which is also the same product was 19.5%, and the total yield of the cresol was 35.7%.

Example 22

The same reaction was carried out as in Example 21 except for changing 3-pentanone to 0.34 g of pinacolin (3,3-dimethyl-2-butanone).

As a result, yield of o-cresol which is an oxidized product of toluene was 20.3%, and p-cresol which is also the same product was 21.9%, and the total yield of the cresol was 42.2%.

Example 23

In 300 ml of a flask were charged 0.50 g of H/β HNO₃ (38) prepared in Example 1, 52.0 g (0.412 mol) of methylenedioxybenzene, 2.16 g (0.022 mol) of pinacolin and 0.02 g of a 85% by weight aqueous phosphoric acid solution, and after the atmosphere was replaced with nitrogen, the temperature of the mixture was raised to 100° C. under stirring. Then, at the same temperature, 0.10 g of a 60% by weight aqueous hydrogen peroxide was added dropwise to the mixture, further added dropwise 0.10 g of the same after 1.5 minutes, 0.10 g after 3 minutes, 0.10 g after 4.5 minutes, 0.10 g after 6 minutes and 0.10 g after 7.5 minutes, and the reaction was carried out for 30 minutes from the initial dropwise addition.

As a result, yield of sesamol (3,4-methylenedioxyphenol) was 28.0%.

Example 24

In 300 ml of a flask equipped with a Dean-Stark moisture receiver manufactured by VIDREX Co. were charged 0.40 g of H/β HNO₃ (38) prepared in Example 1 and 15.00 g of 2,3,6-trimethylphenol, and after the atmosphere was replaced with nitrogen, the temperature of the mixture was raised to 120° C. under stirring. Then, at the same temperature, 0.10 g of a 60% by weight aqueous hydrogen peroxide and 0.40 g of 4-methyl-2-pentanone were added dropwise to the mixture, and after 20 minutes, same amounts of the 60% by weight aqueous hydrogen peroxide and 4-methyl-2-pentanone were further added dropwise to the same, and the reaction was carried out for 30 minutes from the initial dropwise addition. During the reaction, water was continuously removed by the Dean-Stark moisture receiver.

As a result, yield of the 2,3,5-trimethylhydroquinone was 71.9%.

Comparative Example 10

Additional Comparative Example 1

The same reaction was carried out as in Example 25 except for changing the catalyst to H/β (38).

As a result, yield of the 2,3,5-trimethylhydroquinone was 52.1%.

The proton type β zeolite of the present invention can be prepared by a simple and easy method by immersing β zeolite in an aqueous acidic solution. The present proton type β zeolite shows high reactivity at a lower temperature side in the preparation of a phenol compound by oxidizing a benzene compound with a peroxide, and give a phenol compound with high yield.

What is claimed is:

1. A process for preparing at least one phenol compound selected from the group consisting of a compound represented by a formula (3) and a compound represented by a formula (4):

(3)

(4)

wherein R¹ represents a hydroxyl group, a straight or branched alkyl group having 1 to 6 carbon atoms or a straight or branched alkoxy group having 1 to 6 carbon atoms, R² represents a hydrogen atom, a straight or branched alkyl group having 1 to 6 carbon atoms, a straight or branched alkoxy group having 1 to 6 carbon atoms or a halogen atom, n is an integer of 0 to 5, m is an integer of 0 to 5, n+m=0 to 5, a plural number of R¹ or R² may be the same or different from each other, R³ represents a hydrogen atom, a straight or branched alkyl group having 1 to 6 carbon atoms, a straight or branched alkoxy group having 1 to 6 carbon atoms or a halogen atom, p is an integer of 1 or 2 and q is an integer of 0 to 3, which comprises oxidizing at least one benzene compound represented by the formulae (1) and (2):

(1)

(2)

wherein R¹, R², R³, n, m, p and q have the same meanings as defined above, with a peroxide in the presence of a proton type β zeolite in which an acid site showing a desorption peak with a range of ±100° C. with a center of 330° C. exists in a spectrum measured by the ammonia temperature programmed desorption method (NH₃-TPD), and an amount of a strong acid site showing a desorption peak of 500° C. or higher is controlled to 2.5 μmol/g or less, and in the presence of a ketone or a carboxylic acid.

2. The process for preparing a phenol compound according to claim 1, wherein R¹ is an alkoxy group having 1 to 6 carbon atoms, n is 1 and the remaining R² are hydrogen atoms.

3. The process for preparing a phenol compound according to claim 2, wherein the proton type β zeolite is a zeolite on which at least one metal is carried, said at least one metal being selected from the group consisting of an alkaline earth metal; a transition metal; a Group 2B metal selected from the grouP consisting of Zn, Cd and Hg; a Group 3A metal selected from the group consisting of Al, Ga, In and Tl; a Group 4A metals metal selected from the group consisting of Sn and Pb; and a lanthanide metal.

4. The process for preparing a phenol compound according 30 to claim 2, wherein the peroxide is hydrogen peroxide or a ketone peroxide.

5. The process for preparing a phenol compound according to claim 4, which further comprises the oxidizing being carried out in the presence of phosphoric acid.

6. The process for preparing a phenol compound according to claim 2, wherein the peroxide is hydrogen peroxide or a carboxylic acid peroxide.

7. The process for preparing a phenol compound according to claim 6, which further comprises the oxidizing being carried out in the presence of phosphoric acid.

8. The process for preparing a phenol compound according to claim 1, wherein the $R^1$ is a hydroxyl group, n is 1 and at least one of $R^2$ is a straight or branched alkyl group having 1 to 6 carbon atoms or a halogen atom.

9. The process for preparing a phenol compound according to claim 8, wherein the peroxide is hydrogen peroxide or a ketone peroxide.

10. The process for preparing a phenol compound according to claim 1, wherein the process is carried out in the presence of a ketone, said ketone being selected from the group consisting of acetone, methyl ethyl ketone, 2-pentanone, 3-pentanone, 2-hexanone, 2-heptanone, 3-heptanone, 4-heptanone, 2-octanone, 2-nonanone, 3-decanone, 6-undecanone, 2-tridecanone, 7-tridecanone, 2-tetradecanone, 2-pentadecanone, 2-hexadecanone, 2-heptadecanone, 3-octadecanone, 4-nonadecanone, 1-chloro-2-propanone, 1-chloro-3-heptanone, 1-bromo-3-heptanone, 3-methyl-2-butanone, 3-methyl-2-pentanone, 4-methyl-2-pentanone, 3,3-dimethyl-2-butanone, 2,4-dimethyl-3-pentanone, 6-methyl-2-heptanone, 2,6-dimethyl-4-heptanone, 2,2,4,4-tetramethyl-3-heptanone, acetophenone, benzophenone, 1-phenyl-3-propanone, 1-phenyl-1-butanone, 1-phenyl-3-butanone, 1-phenyl-3-pentanone, 1,3, -diphenyl-2-propanone, cyclopentanone, cyclohexanone, cyclododecanone, 2-choorocyclohexanone, 2-ethyl-1-cyclopentanone, 2-methyl-1-cyclohexanone, 2,3-butanedione, 2,4-pentanedione, 2,5-hexanedione, 2,5-dimethyl-3,4-hexanedione, 1,2-diphenylethane-1,2dione and 1,4-cyclohexanedione.

11. The process for preparing a phenol compound according to claim 10, wherein the ketone is 4-methyl-2-pentanone or 3-pentanone.

12. The process for preparing a phenol compound according to claim 10, wherein a molar ratio of the ketone to the peroxide is 0.2:1 to 5:1.

13. The process for preparing a phenol compound according to claim 5, wherein a weight ratio of the phosphoric acid to the phenol is 0.0001:1 to 0.05:1.

14. The process for preparing a phenol compound according to claim 1, wherein the process is carried out in the presence of a carboxylic acid and wherein a molar ratio of the carboxylic acid to the peroxide is 0.2:1 to 5:1.

15. The process for preparing a phenol compound according to claim 14, wherein the carboxylic acid is acetic acid or propanoic acid.

* * * * *